United States Patent [19]
Kullik

[11] Patent Number: 5,763,792
[45] Date of Patent: Jun. 9, 1998

[54] RESPIRATORY FLOW SENSOR

[75] Inventor: Götz Kullik, Lübeck, Germany

[73] Assignee: Drägerwerk AG, Lübeck, Germany

[21] Appl. No.: 791,638

[22] Filed: Jan. 31, 1997

[30] Foreign Application Priority Data

May 3, 1996 [DE] Germany .............. 196 17 738.3

[51] Int. Cl.[6] .................................................. G01F 1/36
[52] U.S. Cl. ............................... 73/861.53; 128/725
[58] Field of Search ..................... 73/861.52, 861.53, 73/861.58, 861.61; 128/725, 726, 727

[56] References Cited

U.S. PATENT DOCUMENTS

| | | | |
|---|---|---|---|
| 3,840,051 | 10/1974 | Akashi et al. | 73/861.52 |
| 3,962,917 | 6/1976 | Terada | 128/725 |
| 4,083,245 | 4/1978 | Osborn | 73/861.53 |
| 4,993,269 | 2/1991 | Guillaume et al. | 73/861.53 |
| 5,060,655 | 10/1991 | Rudolph | 128/725 |

FOREIGN PATENT DOCUMENTS

| | | | |
|---|---|---|---|
| 0 373 886 A1 | 12/1989 | European Pat. Off. | |
| 2558935 | 12/1975 | Germany | 73/861.53 |

*Primary Examiner*—Richard Chilcot
*Assistant Examiner*—Harshad Patel
*Attorney, Agent, or Firm*—McGlew and Tuttle

[57] ABSTRACT

A respiratory flow sensor to be connected between a breathing tube and an endotracheal catheter, which has a flow channel, an orifice, which is formed by a foil recessed in the flow tube, in which an orifice flap is formed by an incision, and has connections to the flow channel on both sides of the orifice to pick up the pressure difference generated over the orifice. The respiratory flow sensor is reusable and makes possible accurate measurement even at low flow rates and low pneumatic resistance. The foil is a metal foil, which is interrupted by a central incision in the area carrying the orifice flap to form two hinge elements which are narrow compared with the width of the orifice flap. A first flow rectifier is arranged in the flow channel between the orifice flap and the connection for the endotracheal catheter.

20 Claims, 5 Drawing Sheets

RESPIRATORY FLOW SENSOR

FIELD OF THE INVENTION

The present invention pertains to a respiratory flow sensor which has a flow tube with a flow channel, which flow tube can be connected for establishing a connection between the breathing tube and the endotracheal catheter, an orifice, which has a foil, which is recessed into the flow tube, covers the cross section of the flow channel, and is incised such that an orifice flap and a surrounding border are formed in the flow channel, wherein the orifice flap is elastically deflectable to offer a variable orifice opening as a function of the oncoming flow, and comprises connections to the flow channel on both sides of the orifice for picking up the pressure difference generated by the orifice.

BACKGROUND OF THE INVENTION

Such a respiratory flow sensor has been known from U.S. Pat. No. 4,083,245. The prior-art respiratory flow sensor has a flow tube, which can be connected to a breathing tube and to an endotracheal catheter and into which a plastic film reaching over the entire cross section of the flow tube is recessed to form an orifice. The film is incised such that an orifice flap and a border are formed. The orifice flap shown has the shape of a rhombus, wherein the incision at one corner of the rhombus is not made complete, so that a connection area is left between the orifice flap and the border. Depending on the oncoming flow, the orifice flap can be deflected in order to bring about an orifice opening that depends on the oncoming flow. Connections are provided before and after the orifice in order to pick up the pressure difference over the orifice.

Pressure difference flow sensors with variable orifices, whose mode of operation is also circumscribed by the terms "variable orifice/moving vane," were developed in medical engineering in order to cover a large range of measurements with sufficient accuracy of measurement. Compared with fixed orifices, relatively high pressure differences are obtained in the case of small flows because of the now very small orifice opening, while relatively smaller pressure differences occur in the case of higher flows because the orifice is now open more widely.

By using a plastic film, in which an orifice flap is formed by an incision, the passage area through the orifice can be set accurately and at a relatively low manufacturing cost with the orifice flap closed, because this passage area is formed precisely by the area of the incision. Higher accuracy and reproducibility of the passage area can thus be reached than when a flexible blocking element is simply located between the outer edge of the blocking element and the inner wall of the flow channel. An exact definition of the passage area is possible in the latter case with difficulty only, because it is compromised by tolerances of the cross-sectional area of the flow channel, of the blocking element, and of the relative orientation of the blocking element in the flow channel. If the orifice is formed by an incision in a film, which is anchored in the flow tube, such tolerance problems are avoided. As a result, sensors with such orifices are, in principle, better suited for measurements in the case of small flows.

Such orifices were previously made of plastic films. The drawback of plastic orifices is, however, the lack of constancy of their mechanical properties under the action of chemicals, eg., disinfectants, over prolonged periods of use. Sensors with plastic orifices are therefore usually intended for single-time use only. The use of metals for orifice bodies is possible, in principle, if the wall thickness is correspondingly reduced to compensate for the higher modulus of elasticity. With a similar cross-sectional area of the flow channel, it would thus be necessary to use wall thicknesses of about 0.01 mm; however, metal foils of such a small thickness cannot be manufactured with a stable shape and stable dimensions.

Metal foils with wall thicknesses greater than 0.025 mm are available with a stable shape, so that it would be possible to manufacture orifices for sterilizable sensors with them. The orifice flap must be held in the flow channel by means of a hinge element to reach an acceptable, low pneumatic resistance at the increased modulus of elasticity. Such a design has been known from EP-A-0 373 886, in which the orifice flap passes over into a narrow web, which is anchored in the flow tube outside the flow channel and acts as a hinge for the orifice. However, with the orifice flap closed, the passage area is defined in this design by the outer edge of the orifice flap and the inner wall of the surrounding flow channel, as a result of which accurate manufacture of a very small passage area is difficult for the above-mentioned reasons.

Another problem for respiratory flow sensors, which are to operate accurately even at low flow rates at a low pneumatic resistance, is the fact that the deflection of the orifice and consequently the orifice opening and the pressure difference over the orifice, which pressure difference is used for the measurement, depend on the flow profile of the air flow in the flow channel. It should be borne in mind, in particular, that the respiratory flow sensor is connected in actual use to tubes, which may assume any bent shape during practical use, which may considerably affect the flow profile in the area of the orifice especially in the case of bending of the thin endotracheal catheter tube shortly before entering the flow channel of the respiratory flow sensor. The most homogeneous distribution possible of the velocities of flow at the orifice is desirable, and this distribution should also be independent from distortions of the flow distribution, from possible backflows and swirls in the area of the entry into the flow channel. A homogenization of the flow profile can be achieved by extending the flow channel before the orifice, on the one hand, in which case a homogenization of the profile takes place due to such an extended inlet section as a result of compensating flows at right angles to the longitudinal axis of the channel. On the other hand, a more uniform flow profile can be obtained by a contraction of the flow channel, i.e., a reduction in its cross-sectional area. However, to achieve a fluidic optimization and consequently independence from the flow profile at the inlet of the respiratory flow sensor, extension of the flow channel requires an inlet section in front of the orifice, which is at least 5 times as large on the side of the breathing tube as the flow tube diameter (cf, e.g., O. Fiedler, *Strömungs- und Durchluβmeβtechnik* [Anemometry and Flow Measurement], Munich; Oldenbourg-Verlag 1992). The flow channel would have to be even longer on the patient's side, because the inflow conditions from the thin and bent endotracheal catheter tube are extremely nonuniform. However, such long flow channel sections increase the dead space in a medically unacceptable manner, i.e., each breath, the patient inhales an excessively large percentage of the gas he exhaled with his preceding breath (pendular breathing). On the other hand, even though a contraction of the flow channel to homogenize the flow profile is highly effective from a fluidic viewpoint, it increases the permanent pressure loss and consequently the airway resistance of the patient in a medically undesired manner. A respiratory flow sensor that operates accurately at low flow rates and with a low pneumatic resistance is therefore needed, especially for applications in children.

SUMMARY AND OBJECTS OF THE INVENTION

The primary object of the present invention is to design a respiratory flow sensor of the type described in the introduction such that it can be reused and such that it makes it possible to perform an accurate measurement of the respiratory flow even at low flow rates and low pneumatic resistance for the patient, possibly independently from the flow conditions in the endotracheal catheter tube.

According to the invention, a respiratory flow sensor is provided which has a flow tube with a flow channel. The flow tube can be connected for establishing a connection between the breathing tube and the endotracheal catheter. An orifice, which has a foil, which is recessed into the flow tube, covers the cross section of the flow channel, and is incised such that an orifice flap and a surrounding border are formed in the flow channel. The orifice flap is elastically deflectable to offer a variable orifice opening as a function of the oncoming flow, and comprises connections to he flow channel on both sides of the orifice for picking up the pressure difference generated by the orifice. The foil is a metal foil which is interrupted by a central incision in the area carrying the orifice flap in order to form two hinge elements. The hinge elements are narrow compared with the width of the orifice flap outside the central incision. A first flow rectifier is arranged in the flow channel between the orifice flap and the connection for the endotracheal catheter.

A second flow rectifier is preferably arranged in the flow channel between the orifice flap and the connection for the breathing tube. The first and second flow rectifiers are preferably formed by a wire screen, each covering the cross section of the flow channel. One or both of the first and second flow rectifiers are preferably designed such that they generate a higher flow resistance in the area of the central axis of the flow channel than at the edge of the flow channel. Preferably one or both of the first and/or second flow rectifiers are provided with a baffle plate each in their centers. One or both of the first and second flow rectifiers preferably comprise a wire screen whose mesh size is smaller in the center than at the edge.

The distance between the first flow rectifier and the orifice is preferably at least as large as the diameter of the flow channel. The distance between the first flow rectifier and the orifice in the flow channel may approximately correspond to twice the diameter of the said flow channel. The length of the flow channel before the first flow rectifier is preferably at least as large as the diameter of the flow channel. The cross-sectional area of the flow channel at the beginning of the inlet section preferably decreases from the endotracheal catheter before the first flow rectifier in the direction of the first flow rectifier.

An orifice flap, which comprises a metal foil, is used in the respiratory flow sensor according to the present invention. The metal foil is incised such that an orifice flap and a surrounding border are formed, wherein the area of the metal foil connecting the orifice flap to the border is interrupted by a central incision, so that two hinge elements, which are narrow compared with the width of the orifice flap, are present. A flow rectifier, which ensures the homogenization of the flow profile at the orifice, is arranged in the flow channel in front of the orifice on the side of the endotracheal catheter. A respiratory flow sensor with low pneumatic resistance, which operates accurately even at low flow rates, and is insensitive to changes in the flow conditions, e.g., those caused by a different position of the breathing tube and the endotracheal catheter tube, is created by the combination of the measures according to the present invention. The passage area with the orifice flap closed can be very small and be made very accurate, because the incision in the metal foil to form the orifice flap can be made very narrow and very accurate. Furthermore, the elastic resistance is reduced by the further incision in the area connecting the orifice flap to the border due to the formation of two narrow webs of the metal foil to the extent that the pneumatic resistance of the orifice will be low. By forming two hinge elements outside the center of the orifice flap, the risk of torsional vibrations of the orifice flap, which may lead to a stressing of the material and to undesired sound radiation, are avoided. Homogenization of the flow profile at the orifice, which makes the respiratory flow sensor independent from the variable flow conditions, especially in the endotracheal catheter tube and at the entry into the flow channel, is achieved by the arrangement of a flow rectifier in front of the orifice on the side of the endotracheal catheter. The combination of the measures according to the present invention leads to a considerably improved respiratory flow sensor.

In an advantageous embodiment, a flow rectifier may also be arranged in front of the orifice flap on the side of the breathing tube. However, the flow conditions are usually less critical on the side of the breathing tube, because these tubes usually have a larger diameter than the endotracheal catheter tube.

The flow rectifiers may be formed, e.g., by a wire screen covering the flow channel, and it is advantageous to increase the flow resistance in the middle of the flow rectifier, e.g., by a baffle plate arranged in the middle or by a smaller mesh size in the center, in order to dampen the flow velocity peaks located in the middle and to ensure a homogenization of the flow profile. The first flow rectifier is advantageously arranged for this purpose at least at a distance from the orifice that corresponds to the diameter of the flow channel, and it is advantageously located at a distance corresponding to twice that diameter. Optimization of the flow conditions at the orifice is achieved as a result.

The metal foil of the orifice preferably consists of a copper alloy, titanium, or a titanium alloy, or stainless steel.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
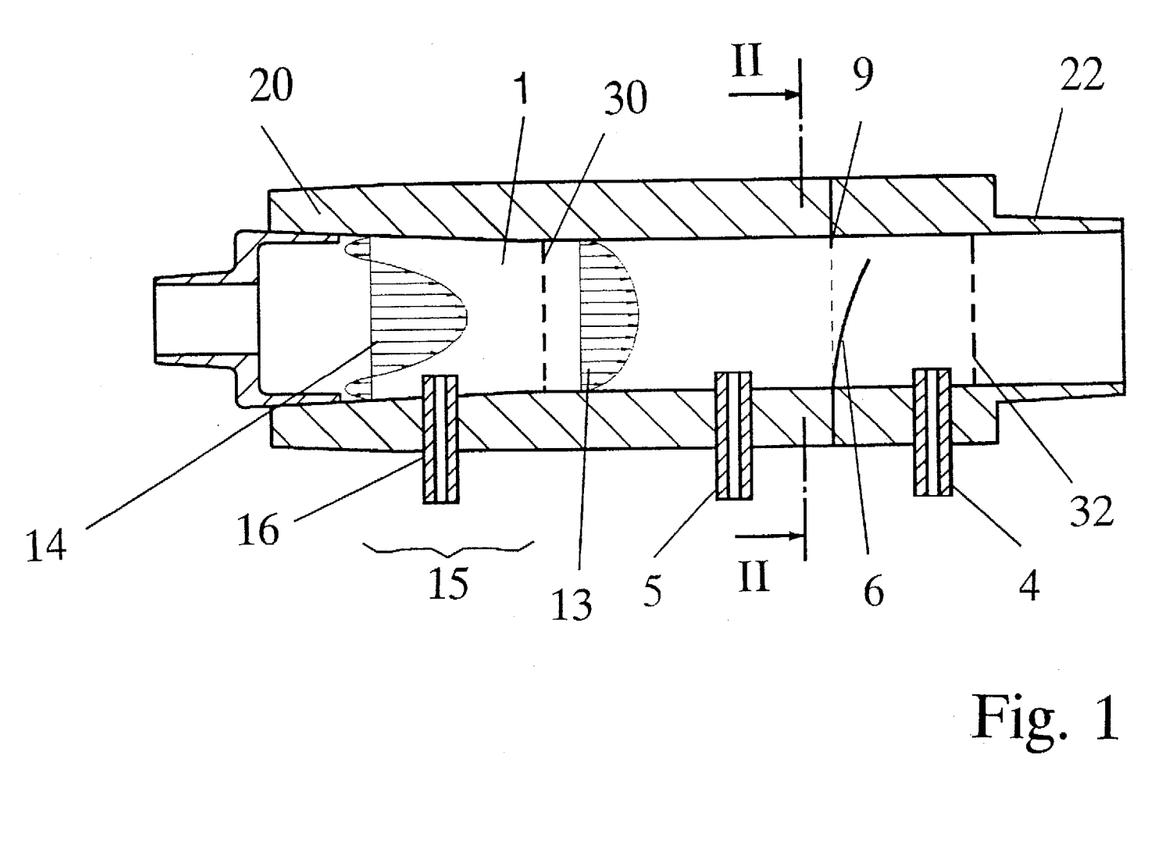
FIG. 1 is a cross sectional view through the respiratory flow sensor according to the invention.

The respiratory flow sensor shown in FIG. 1 has a flow tube 20 with a flow channel 1. On the side that is the left-hand side in the view in FIG. 1, the respiratory flow sensor is connected to an endotracheal catheter tube via an ISO cone 15. The breathing tube is to be connected on the opposite side. An orifice 6, 9 with variable opening surface is provided in the flow channel. Connections 4, 5, at which the pressure difference over the orifice can be picked up, are present on both sides of the orifice 6, 9.

Figure 2:
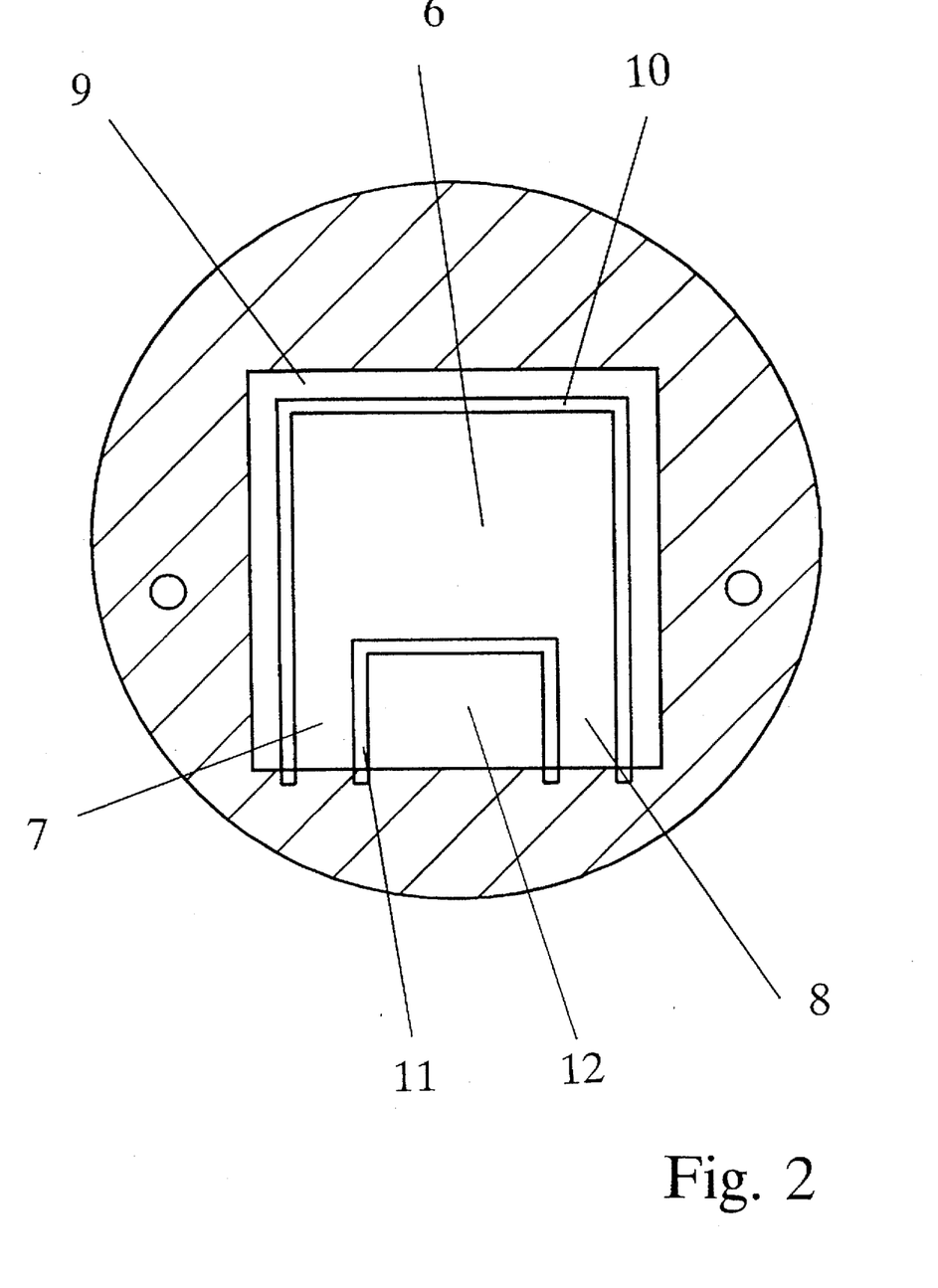
FIG. 2 is a sectional view taken along line II—II of FIG. 1.

The top view of the orifice 6, 9 is shown in FIG. 2. The orifice comprises a metal foil, e.g., a stainless steel foil, which is divided by a flap incision 10 into an orifice flap 6 and a border 9. The metal foil is firmly recessed in the surrounding flow tube. The necessary flexibility of the orifice flap is achieved by the middle part of the area of the metal foil carrying the orifice flap 6 being divided by another incision 11, so that two hinge elements 7 and 8 of the metal foil are left in place and separated from a base area 12, which carry the orifice flap 6. The hinge elements 7 and 8 are advantageously located at the greatest possible distance from one another in order to avoid torsional vibrations of the orifice flap.

Due to the orifice flap 6 and the border 9 being formed by an incision from a metal foil, the position of the orifice flap 6 in its border 9 is exactly defined and is independent from tolerances during the assembly of its individual components. It is possible due to this design to make the gap or the incision 10 between the orifice flap 6 and the wall 9 very small (shown greatly enlarged in FIG. 2). As a result, only a very small passage area, namely, that of the incisions 10, 11, is open in the case of very small flows, so that a relatively great pressure difference is obtained over the orifice in the case of small flows. This property is especially advantageous, because the small flows present in the case of the respiration (or artificial respiration) of children can be measured with sufficient accuracy. The characteristic of a respiratory flow sensor according to the present invention with such an orifice is shown in FIG. 3.

The incisions 10, 11 may be prepared by, e.g., wire-EDM or laser cutting, and etching is also possible in the case of some metals. The gap widths of 0.05 to 0.1 mm that can thus be obtained are substantially smaller than the gap widths of about 0.6 mm that can be obtained by the installation of individual parts, so that the desired stronger signals are available with the respiratory flow sensor according to the present invention at smaller flows than in prior-art respiratory flow sensors.

The unit consisting of the orifice flap 6 and the border 9 may be made of, e.g., corrosion-resistant steel; it is especially advantageous to produce it from a metal with a low modulus of elasticity. It is possible to use, e.g., various copper alloys, which are used as spring materials for switches and plugs in electrical engineering, or titanium and titanium alloys. These materials have strength characteristics similar to those of steel at about half the modulus of elasticity, so that it is possible to prepare orifices with a wall thickness of about 0.025 mm in geometries that require no cross section expansion and whose hinge elements can be made so wide that there is no risk of plastic deformation. Furthermore, it is advantageous for the metals suggested above not to be magnetic, so that such a respiratory flow sensor can also be used in the vicinity of a nuclear spin tomograph. The low density is also advantageous in the case of titanium, because the lower mass inertia of the orifice flap associated with it leads to higher dynamics of the measurement. It is also advantageous in the case of titanium that it is physiologically harmless as an implant material and is therefore especially suitable for use in a medical respiratory flow sensor.

Figure 3:
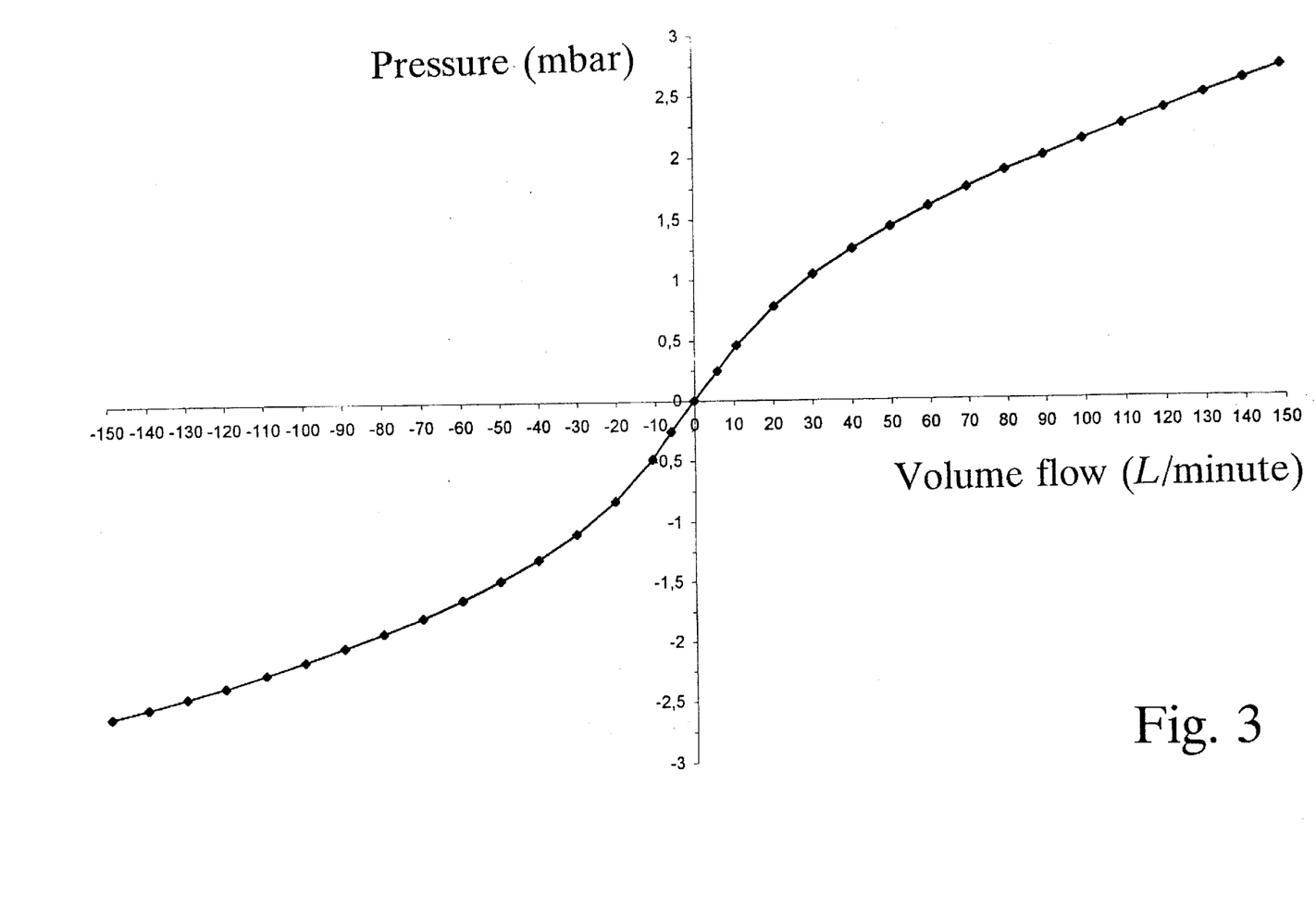
FIG. 3 is a diagram showing the dependence of the pressure over the orifice on the volume flow through the respiratory flow sensor.

FIG. 3 shows the pressure difference over the orifice as a function of the volume flow through the respiratory flow sensor according to the present invention with a titanium orifice. The relatively higher sensitivity at low volume flows compared with higher volume flows is clearly recognizable.

The connections 4 and 5 needed to pick up the pressure difference over the orifice are formed by small tubes, which extend into the flow channel 1 on both sides of the orifice. The connections 4 and 5 are arranged such that the measured value will be as high as possible compared with the permanent pressure loss. It is advantageous in this connection that the ends of the small tubes extend into the flow channel 1, because water of condensation that may possibly be formed in the flow tube thus cannot flow into the connections.

The function of the respiratory flow sensor depends, in principle, on the flow profile at the orifice, i.e., different oncoming flows at equal volume flow lead to different pressure distributions at the orifice and therefore to different pressure difference measured values and consequently to errors of measurement due to different velocity distributions.

It is therefore ensured in the respiratory flow sensor according to the present invention that the flow profile at the orifice always has the same velocity distribution. Extensively uniform flow velocity distribution 13 behind the first flow rectifier 30 is desired. After the flow from the endotracheal catheter tube enters the flow channel 1, there is a highly inhomogeneous flow distribution 14, which even has backflows and swirls as a consequence of the expansion of the cross section. By providing the first flow rectifier 30 in the flow channel, homogenization of the flow profile is achieved. Components such as perforated orifices, laminators, screens, and baffle plates may be used as flow rectifiers.

Figure 5:
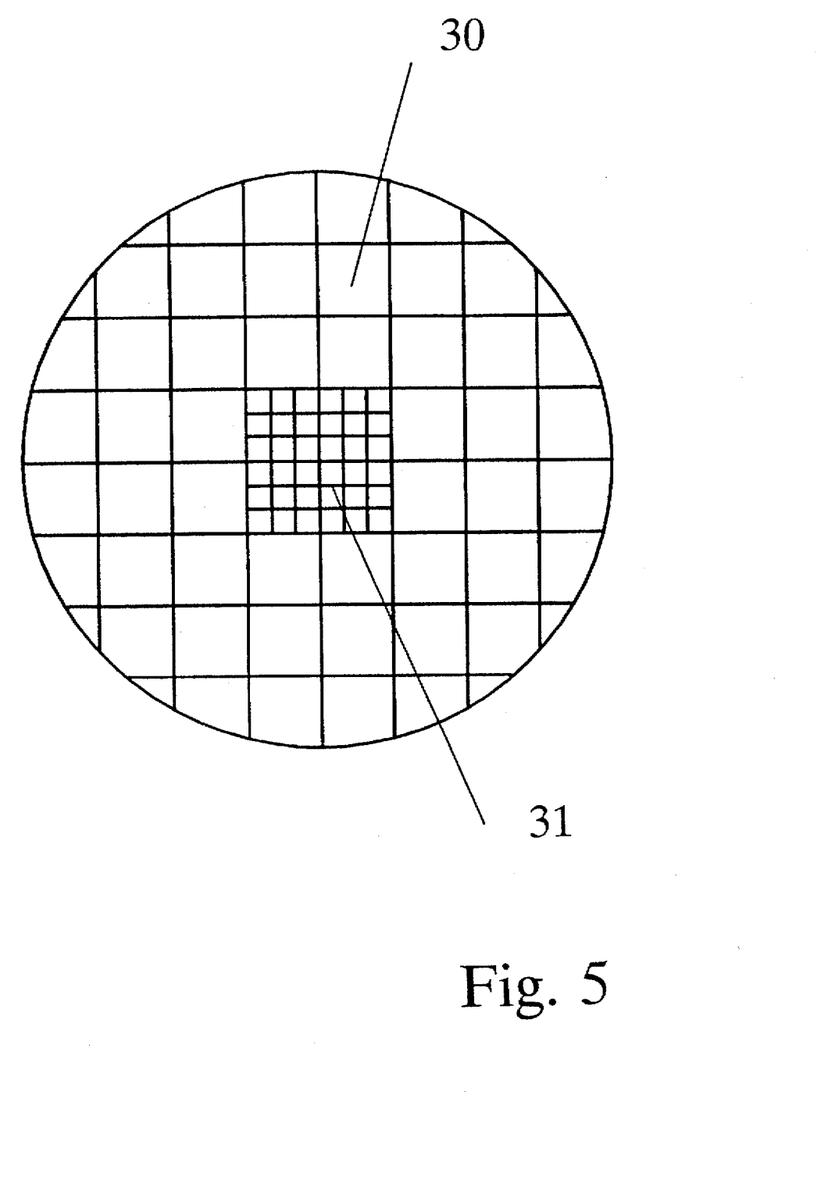
FIG. 5 is the top view of a flow rectifier.

FIG. 5 shows the top view of a flow rectifier 30, which consists of a wire mesh. Since the flow exits from the thin endotracheal catheter in the form of a bundled jet of air, it is meaningful to design the flow rectifier 30 such that it has an increased flow resistance in the middle in order to decelerate the jet and to homogenize the profile. For example, a baffle plate may be fastened in the middle of the screen. However, the permanent pressure loss is markedly increased as a result, so that it is advantageous to arrange a second, finer screen 31 in the middle of the flow rectifier instead of a closed plate, as a result of which homogenization of the flow profile can be achieved at a relatively low airway resistance. Good results are obtained with a tube diameter of, e.g., 15 mm with a combination of wire mesh with a mesh size of about 2.5 mm on the outside and about 0.8 mm in the central area of the screen 31.

In the embodiment shown, the necessary inlet section between the flow rectifier 30 and the orifice 6, 9 is about 30 mm, i.e., approximately twice the diameter of the flow channel. The distance 15 between the endotracheal catheter pipe branch and the first flow rectifier 30 is about 15 mm, i.e., about equal to the tube diameter. The length must be selected as required by the built-in components (e.g., a draw-off connection 16 or the optical windows 17 and 18 in the embodiment according to FIG. 4).

The disturbances in the flow profile are smaller on the apparatus side with the connection 22 for the breathing tube, because only slightly different profiles occur on this side as a consequence of the relatively large cross section of the breathing tube and of the tube connector. A second flow rectifier 32, which is arranged in the flow channel 1 as a simple, coarse rectifying screen at a distance of about 15 mm from the orifice, i.e., approximately at a distance equaling the tube diameter, is therefore located on the side of the orifice facing the breathing tube.

The provision of the first and second flow rectifiers 30 and 32 additionally offers the advantage that the orifice is protected, because it cannot be encased into the sensor or cannot be inserted with a tool. Another advantage is encountered in the case of rupture of the orifice. Should the orifice flap be torn off, it is retained by the screen and cannot proceed either to the patient or to the respirator.

A connection 16 for drawing off breathing gas for a gas analysis is integrated within the flow tube. The gas composition is used, among other things, to correct the measured value. The pressure difference measured over the orifice is a function of the density of the gas at a fixed volume flow. The density of the gas is determined from the gas analysis and is corrected corresponding to the value of the pressure difference. This correction is also possible, in principle, in the case of prior-art sensors based on the "variable orifice/moving vane" principle, but a separate component is necessary for connecting a draw-off tube. The structural unity of the flow tube and the draw-off connection 16 is especially advantageous in the sensor according to the present invention, because a connection point and a dead space are thus eliminated.

Figure 4:
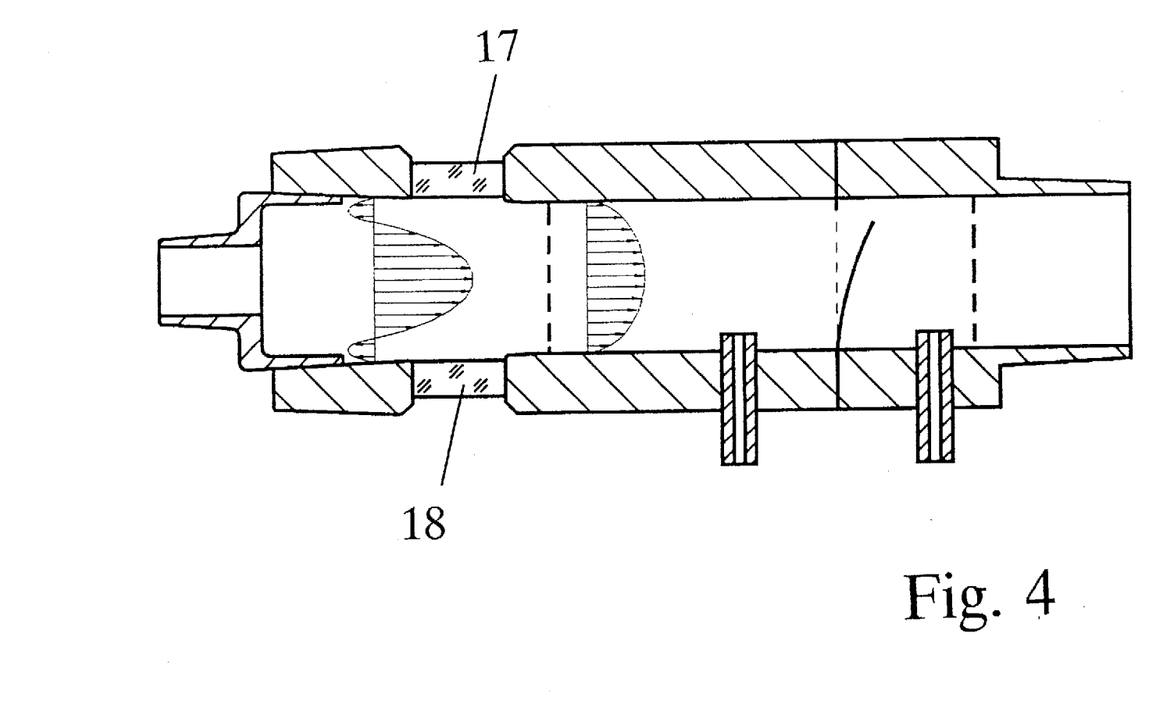
FIG. 4 is a view similar to FIG. 1 of an alternative embodiment of the respiratory flow sensor.

Provisions are also made for equipping the respiratory flow sensor according to FIG. 4 with optical windows 17 and 18, so that the breathing gas and the gas composition can be measured directly in the main flow by means of a suitable infrared spectroscopic measuring instrument. Such measuring instruments have been known from $CO_2$ measurement and are currently being developed for a complete breathing gas analysis.

The respiratory flow sensor shown in FIG. 1 has a slight taper of its cross-sectional area or contraction on the side facing the endotracheal catheter, as a result of which a homogenization of the flow profile is also brought about.

While specific embodiments of the invention have been shown and described in detail to illustrate the application of the principles of the invention, it will be understood that the invention may be embodied otherwise without departing from such principles.

What is claimed is:

1. A respiratory flow sensor for use with a breathing tube and an endotracheal catheter, comprising:

a flow tube with a flow channel, said flow tube being connectable for establishing a connection between the breathing tube and the endotracheal catheter;

orifice means provided in said flow tube for defining an orifice, said orifice means including a foil, which is recessed into the flow tube, substantially covers the cross section of the flow channel, and is incised to form a flap incision such that an orifice flap and a surrounding border are formed in the flow channel, said orifice flap being elastically deflectable to offer a variable orifice opening as a function of an oncoming respiratory gas flow, said foil being a metal foil which is interrupted by a central incision in an area forming said orifice flap to define two hinge elements, said hinge elements being narrow compared with a width of said orifice flap outside said central incision;

a flow rectifier arranged in said flow channel between said orifice flap and a connection for the endotracheal catheter;

another flow rectifier arranged in said flow channel between said orifice flap and the connection for the breathing tube;

a connection to the flow channel on each side of said orifice for sensing a pressure difference generated across said orifice.

2. A respiratory flow sensor in accordance with claim 1, wherein at least one of said flow rectifier and said another flow rectifier are designed such that they generate a higher flow resistance in an area of a central axis of said flow channel than at an edge of said flow channel.

3. A respiratory flow sensor in accordance with claim 1, wherein at least one of said flow rectifier and said another flow rectifier are provided with a baffle plate in a center thereof.

4. A respiratory flow sensor in accordance with claim 1, wherein at least one of said flow rectifier and said another flow rectifier comprise a wire screen with a mesh size smaller in a center than at an edge.

5. A respiratory flow sensor in accordance with claim 1, wherein a distance between said flow rectifier and said orifice is at least as large as a diameter of said flow channel.

6. A respiratory flow sensor in accordance with claim 5, wherein a distance between said flow rectifier and said orifice in said flow channel approximately corresponds to twice a diameter of said flow channel.

7. A respiratory flow sensor in accordance with claim 1, wherein a length of said flow channel before said flow rectifier is at least as large as a diameter of said flow channel.

8. A respiratory flow sensor in accordance with claim 1, wherein a cross-sectional area of said flow channel at a beginning of an inlet section decreases from the endotracheal catheter before said flow rectifier in the direction of said flow rectifier.

9. A respiratory flow sensor in accordance with claim 1, wherein said metal foil is made of a copper alloy;

said flow rectifier is formed of a wire screen with a mesh size smaller in a center than at an edge;

said another flow rectifier is a simple coarse rectifying screen.

10. A respiratory flow sensor in accordance with claim 1, wherein said metal foil is made of one of titanium and titanium alloy.

11. A respiratory flow sensor in accordance with claim 1, wherein said metal foil is made of stainless steel.

12. A respiratory flow sensor in accordance with claim 1, wherein:

said flow rectifier and said another flow rectifier are formed by a wire screen with each flow rectifier covering a flow cross section of said flow channel.

13. A respiratory flow sensor, comprising:

a flow tube with a flow channel having a first end and a second end;

a metal foil positioned in said flow tube and being supported by said flow tube, said metal foil defining a passageway between said first and second end of said flow tube, said passageway including a flap incision forming an orifice flap and a surrounding border in the flow channel, said passageway also including a central incision in an area forming said orifice flap to define two hinge elements, said hinge elements having a width which is narrower than a portion of said flap adjacent to said central incision and adjacent to said hinge elements, said central incision increasing elastic deflectability of said orifice flap to offer a variable orifice opening as a function of oncoming respiratory gas flow;

a flow rectifier arranged in said flow channel between said orifice flap and one of said ends of said flow tube;

another flow rectifier arranged in said flow channel between said orifice flap and another of said ends of said flow tube;

a connection to the flow channel on each side of said passageway for sensing a pressure difference generated across said passageway.

14. A respiratory flow sensor in accordance with claim 13, wherein at least one of said flow rectifier and said another flow rectifier are designed such that they generate a higher flow resistance in an area of a central axis of said flow channel than at an edge of said flow channel.

15. A respiratory flow sensor in accordance with claim 13, wherein at least one of said flow rectifier and said another flow rectifier comprise a wire screen with a mesh size smaller in a center than at an edge.

16. A respiratory flow sensor in accordance with claim 15, wherein:

said first end of said flow tube is connectable to an endotracheal catheter, and said second end is connectable to a breathing tube, said endotracheal catheter having a diameter smaller than a diameter of said breathing tube;

a length of said flow channel before said flow rectifier is at least as large as a diameter of said flow channel;

a distance between said flow rectifier and said metal foil in said flow channel approximately corresponds to twice a diameter of said flow channel;

a distance between said another flow rectifier and said metal foil is at least as large as a diameter of said flow channel;

a cross-sectional area of said flow channel at a beginning of an inlet section decreases from the endotracheal catheter before said flow rectifier in the direction of said flow rectifier;

said flow tube includes an optical window for measuring gas composition by a spectroscopic measuring instrument.

17. A respiratory flow sensor in accordance with claim 13, wherein:

said central incision separates said orifice flap from a base area of said metal foil, said base area of said metal foil extending into said flow channel and defining a portion of said passageway.

18. A respiratory flow sensor in accordance with claim 13, wherein:

said flow rectifier and said another flow rectifier are formed by a wire screen with each flow rectifier covering a flow cross section of said flow channel.

19. A method for forming a respiratory flow sensor, the method comprising the steps of:

providing a flow tube with a flow channel having a first end and a second end;

providing a metal foil;

incising said metal foil to define a flap incision forming an orifice flap and a surrounding border;

incising said metal foil to define a central incision in an area forming said orifice flap to define two hinge elements, said hinge elements having a width which is narrower than a portion of said flap adjacent to said central incision and adjacent to said hinge elements, said central incision increasing elastic deflectability of said orifice flap to offer a variable orifice opening as a function of oncoming respiratory gas flow;

positioning said metal foil in said flow tube and connecting said metal foil to said flow tube to have said flap and central incision define a passageway between said first and second end of said flow tube, said positioning and connecting of said metal foil placing said surrounding border in said flow channel;

positioning a flow rectifier in said flow channel between said metal and one of said ends of said flow tube;

positioning another flow rectifier in said flow channel between said metal and another of said ends of said flow tube;

positioning a connection to said flow channel on each side of said passageway for sensing a pressure difference generated across said passageway.

20. A method in accordance with claim 19, wherein:

said incising in performed by one of laser or wire-EDM cutting.

* * * * *